(12) United States Patent
Brisken et al.

(10) Patent No.: US 7,848,815 B2
(45) Date of Patent: *Dec. 7, 2010

(54) IMPLANTABLE TRANSDUCER DEVICES

(75) Inventors: Axel F. Brisken, Fremont, CA (US);
Mark W. Cowan, Fremont, CA (US);
Debra S. Echt, Woodside, CA (US);
Richard E. Riley, Palo Alto, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/554,199

(22) Filed: Sep. 4, 2009

(65) Prior Publication Data
US 2009/0319006 A1    Dec. 24, 2009

Related U.S. Application Data

(63) Continuation of application No. 11/315,524, filed on Dec. 21, 2005, now Pat. No. 7,606,621.

(60) Provisional application No. 60/689,606, filed on Jun. 9, 2005, provisional application No. 60/639,027, filed on Dec. 21, 2004, provisional application No. 60/639,056, filed on Dec. 21, 2004.

(51) Int. Cl.
*A61N 1/00* (2006.01)
(52) U.S. Cl. ........................................ 607/33
(58) Field of Classification Search ............... 250/221; 329/311; 342/202; 356/461; 600/437, 439, 600/443, 463; 623/1.11; 607/32, 33
See application file for complete search history.

(56) References Cited

U.S. PATENT DOCUMENTS

| 3,659,615 A | 5/1972 | Enger |
| 3,693,627 A | 9/1972 | Berkovits |
| 3,698,398 A | 10/1972 | Berkovits |
| 3,735,756 A | 5/1973 | Richards et al. |
| 3,832,994 A | 9/1974 | Bicher et al. |
| 3,857,382 A | 12/1974 | Williams et al. |
| 3,939,844 A | 2/1976 | Peuignot |

(Continued)

FOREIGN PATENT DOCUMENTS

DE    4330680 A1    3/2005

(Continued)

OTHER PUBLICATIONS

Abraham et al., For the MIRACLE study group, "Cardiac Resynchronization in Chronic Heart Failure," N Engl J Med, 2002;346:1845-53.

(Continued)

*Primary Examiner*—George Manuel
*Assistant Examiner*—Robert N Wieland
(74) *Attorney, Agent, or Firm*—Townsend and Townsend and Crew LLP

(57) ABSTRACT

Receiver-stimulators comprise a nearly isotropic transducer assembly, demodulator circuitry, and at least two tissue contacting electrodes. Use of near isotropic transducers allows the devices to be implanted with less concern regarding the orientation relative to an acoustic energy source. Transducers or transducer elements having relatively small sizes, typically less than ½ the wavelength of the acoustic source, enhance isotropy. The use of single crystal piezoelectric materials enhance sensitivity.

18 Claims, 17 Drawing Sheets

U.S. PATENT DOCUMENTS

| | | | |
|---|---|---|---|
| 3,942,534 A | 3/1976 | Allen et al. | |
| 4,181,133 A | 1/1980 | Kolenik et al. | |
| 4,256,115 A | 3/1981 | Bilitch | |
| 4,265,228 A | 5/1981 | Zoll | |
| 4,280,502 A | 7/1981 | Baker, Jr. et al. | |
| 4,561,442 A | 12/1985 | Vollmann et al. | |
| 4,577,633 A | 3/1986 | Berkovits et al. | |
| 4,651,716 A | 3/1987 | Forester et al. | |
| 4,690,144 A | 9/1987 | Rise et al. | |
| 4,830,006 A | 5/1989 | Haluska et al. | |
| 5,018,523 A | 5/1991 | Bach, Jr. et al. | |
| 5,063,928 A | 11/1991 | Grevis | |
| 5,103,129 A | 4/1992 | Slayton et al. | |
| 5,113,859 A | 5/1992 | Funke | |
| 5,165,403 A | 11/1992 | Mehra | |
| 5,170,784 A | 12/1992 | Ramon | |
| 5,174,289 A | 12/1992 | Cohen | |
| 5,186,177 A * | 2/1993 | O'Donnell et al. | 600/463 |
| 5,193,539 A | 3/1993 | Schulman et al. | |
| 5,292,338 A | 3/1994 | Bardy | |
| 5,377,166 A | 12/1994 | Kuhn | |
| 5,405,367 A | 4/1995 | Schulman et al. | |
| 5,411,535 A * | 5/1995 | Fujii et al. | 607/32 |
| 5,433,731 A | 7/1995 | Hoegnelid et al. | |
| 5,590,657 A * | 1/1997 | Cain et al. | 600/439 |
| 5,674,251 A | 10/1997 | Combs et al. | |
| 5,749,909 A | 5/1998 | Schroeppel et al. | |
| 5,751,539 A | 5/1998 | Stevenson et al. | |
| 5,757,104 A | 5/1998 | Getman | |
| 5,766,227 A | 6/1998 | Nappholz et al. | |
| 5,800,464 A | 9/1998 | Kieval | |
| 5,814,089 A | 9/1998 | Stokes et al. | |
| 5,817,130 A | 10/1998 | Cox et al. | |
| 5,844,349 A | 12/1998 | Oakley et al. | |
| 5,871,506 A | 2/1999 | Mower | |
| 5,879,303 A | 3/1999 | Averkiou et al. | |
| 5,935,158 A | 8/1999 | Holmstrom et al. | |
| 5,978,204 A | 11/1999 | Stevenson | |
| 5,998,910 A | 12/1999 | Park et al. | |
| 6,037,704 A | 3/2000 | Welle | |
| 6,070,101 A | 5/2000 | Struble et al. | |
| 6,078,837 A | 6/2000 | Peterson et al. | |
| 6,110,098 A | 8/2000 | Renirie et al. | |
| 6,223,079 B1 | 4/2001 | Bakels et al. | |
| 6,233,484 B1 | 5/2001 | Ben-Haim et al. | |
| 6,264,611 B1 | 7/2001 | Ishikawa et al. | |
| 6,330,475 B1 | 12/2001 | Renirie et al. | |
| 6,366,816 B1 | 4/2002 | Marchesi | |
| 6,408,205 B1 | 6/2002 | Renirie et al. | |
| 6,424,234 B1 | 7/2002 | Stevenson | |
| 6,425,869 B1 | 7/2002 | Rafter et al. | |
| 6,439,236 B1 | 8/2002 | Porter et al. | |
| 6,445,953 B1 | 9/2002 | Bulkes et al. | |
| 6,464,680 B1 | 10/2002 | Brisken et al. | |
| 6,527,729 B1 | 3/2003 | Turcott | |
| 6,534,895 B2 | 3/2003 | Kadota et al. | |
| RE38,119 E | 5/2003 | Mower | |
| 6,628,989 B1 | 9/2003 | Penner et al. | |
| 6,645,145 B1 | 11/2003 | Dreschel et al. | |
| 6,647,292 B1 | 11/2003 | Bardy et al. | |
| 6,654,638 B1 | 11/2003 | Sweeny | |
| 6,671,547 B2 | 12/2003 | Lyster et al. | |
| 6,707,230 B2 | 3/2004 | Smith et al. | |
| 6,721,597 B1 | 4/2004 | Bardy et al. | |
| 6,728,576 B2 | 4/2004 | Thompson et al. | |
| 6,754,528 B2 | 6/2004 | Bardy et al. | |
| 6,754,531 B1 | 6/2004 | Kroll et al. | |
| 6,764,446 B2 | 7/2004 | Wolinsky et al. | |
| 6,788,974 B2 | 9/2004 | Bardy et al. | |
| 6,834,204 B2 | 12/2004 | Osteroff et al. | |
| 6,856,835 B2 | 2/2005 | Bardy et al. | |
| 6,970,742 B2 | 11/2005 | Mann et al. | |
| 7,006,864 B2 | 2/2006 | Echt et al. | |
| 7,050,849 B2 | 5/2006 | Echt et al. | |
| 7,160,258 B2 | 1/2007 | Imran et al. | |
| 7,184,830 B2 | 2/2007 | Echt et al. | |
| 7,283,874 B2 * | 10/2007 | Penner | 607/33 |
| 7,349,740 B2 | 3/2008 | Soykan et al. | |
| 7,489,967 B2 | 2/2009 | Von Arx et al. | |
| 7,558,631 B2 | 7/2009 | Cowan et al. | |
| 7,606,621 B2 | 10/2009 | Brisken et al. | |
| 7,610,092 B2 | 10/2009 | Cowan et al. | |
| 2002/0077673 A1 | 6/2002 | Penner et al. | |
| 2003/0013974 A1 | 1/2003 | Natarajan et al. | |
| 2003/0069625 A1 | 4/2003 | Ley et al. | |
| 2004/0015104 A1 | 1/2004 | Goldberger | |
| 2004/0162501 A1 | 8/2004 | Imran | |
| 2004/0172083 A1 | 9/2004 | Penner | |
| 2004/0204744 A1 | 10/2004 | Penner et al. | |
| 2004/0260346 A1 | 12/2004 | Overall et al. | |
| 2005/0070962 A1 | 3/2005 | Echt et al. | |
| 2006/0009831 A1 | 1/2006 | Lau et al. | |
| 2006/0161061 A1 | 7/2006 | Echt et al. | |
| 2006/0224067 A1 | 10/2006 | Giftakis et al. | |
| 2006/0241701 A1 | 10/2006 | Markowitz et al. | |
| 2007/0032749 A1 | 2/2007 | Overall et al. | |
| 2007/0232936 A1 | 10/2007 | Mann et al. | |
| 2009/0326601 A1 | 12/2009 | Brisken et al. | |

FOREIGN PATENT DOCUMENTS

| | | |
|---|---|---|
| WO | WO 99/61058 A1 | 12/1999 |
| WO | WO 03/070323 A1 | 8/2003 |

OTHER PUBLICATIONS

ACC/AHA Task Force on Practice Guidelines, "Evaluation and Management of Chronic Heart Failure in the Adult," JACC 2002;38:2101-13.

Allessie et al., "Regional Control of Atrial Fibrillation by Rapid Pacing in Conscious Dogs," Circulation 1991;84:1689-97.

Ansalone et al., "Bi-ventricular Pacing I Heart Failure:Back to Basics in the Pathophysiology of Left Bundle Branch Block to Reduce the Number of Nonresponders," Am J Cardiol 2003;91:55F-61F.

Auricchio et al., "Cardiac Resynchronization Therapy: Current State of the Art," Circulation 2004;109:300-307.

Bardy et al., "The Totally Subcutaneous ICD System (the S-ICD)," PACE. 2002; 24,578.

Becker et al, "Suppression of Atrial Fibrillation by Multisite and Septal Pacing in a Novel Experimental Model", Cardiovascular Research 2001;54(2):476-481.

Bradley et al., "Cardiac Resynchronization and Death from Progressive Heart Failure: A Meta-Analysis of Randomized Controlled Trials," JAMA 2003;289:730-740.

Camm et al., Chapter 6: Nonpharmaceutical treatment of atrial fibrillation, In Atrial Fibrillation. Facts from Yesterday—Ideas for tomorrow. Futura Publishing Company, Inc., Armonk, NY, 1994, pp. 125-147.

Dalecki et al., "Effects of Pulsed Ultrasound on the Frog Heart: I. Thresholds for Changes in Cardiac Rhythm and Aortic Pressure," Ultrasound in Med. & Biol. 1993; 19:385-390.

Dalecki et al., "Effects of Pulsed Ultrasound on the Frog Heart: II. An Investigation of Heating as a Potential Mechanism," Ultrasound in Med. & Biol. 1993; 19:391-398.

Dalecki et al., "Thresholds for premature ventricular contractions in frog hearts exposed to lithotripter fields," Ultrasound in Med. & Biol. 1991; 17:341-346.

Daoud et al., "Implantation Techniques and Chronic Lead Parameters of Biventricular Pacing Dual-chamber Defibrillators," J Cardiovasc Electrophysiology 2002; 13:964-970.

Daubert et al., "Permanent Left Ventricular Pacing With Transvenous Leads Inserted Into the Coronary Veins," PACE 1998;21;239-245.

Daubert et al., "Use of Specifically Designed Coronary Sinus Leads for Permanent Left Ventricular Pacing: Preliminary Experience," PACE, 1997; 20: II-NASPE Abstract 17, Apr. 1997.

David Trial Investigators, "The Dual Chamber and VVI Implantable Defibrillator (DAVID) Trial," JAMA 2002;288:3115-3123.

Deshmukh et al. "Direct His-bundle pacing: present and future," PACE 2004;27 [Pt.II]:862-70.

Ellenbogen et al., "Detection and Management of an Implantable Cardioverter Defibrillator Lead Failure," JACC. 2003;41:73-80.

Feldman et al, "Comparison of medical therapy, resynchronization and defibrillation therapies in heart failure trial (COMPANION)," Presented at ACC 2003 Late Breaking Clinical Trials, 1 page.

Franz, "Mechano-electrical feedback in ventricular myocardium," Cardiovascular Research. 1996; 32:15-24.

Gregoratos et al., ACC/AHA/NASPE 2002 guideline update for implantation of cardiac pacemakers and antiarrhythmia devices: a report of the American College of Cardiology/American Heart Association Task Force on Practice Guidelines (ACC/AHA/NASPE Committee to Update the 1998 Pacemaker Guidelines). Circulation. 2002; 106:2145-2161.

Hu et al., "Stretch-Activated Ion Channels in the Heart," J. Mol. Cell Cardiol. 1997; 29:1511-1523.

Johnson et al., "Adaptive Pacing During Ventricular Fibrillation," PACE 2003;26:1824-36.

Kalman J.M. et al, "Regional Entrainment of Atrial Fibrillation in Man", J Cardiovasc Electrophysiol 1991;7:867-76.

Kass et al., "Improved Left Ventricular Mechanics from Acute VDD Pacing in Patients with Dilated Cardiomyopathy and Ventricular Conduction Delay," Circulation 1999;99:1567-73.

Kenknight B.H. et al, "Regional Capture of Fibrillating Ventricular Myocardium" Circ Res 1999;77:849-55.retrieve from the Internet: <<http://circres.ahajournals.org/cgi/content/full/77/4/849>>.

Kohl et al., Stretch-Induced Changes in Heart Rate and Rhythm: Clinical Observations, Experiments and Mathematical Models. Progress in Biophysics & Molecular Biology, 1999; 71:91-138.

Kohl et al., "Sudden Cardiac Death by Commotio Cordis: Role of Mechano-Electrical Feedback," Cardiovascular Research, 2001; 50:280-289.

Leclercq et al, "Is Dual Site Better than Single Site Atrial Pacing in the Prevention of Atrial Fibrillation?" PACE 2000;23:2102-7.

Leclercq et al., "Systolic Improvement and Mechanical Resynchronization does not Require Electrical Synchrony in the Dilated Failing Heart with Left Bundle-Branch Block", Circulation 2002;106:1760-1763.

Leclerq et. al., "Acute Hemodynamic Effects of Biventricular DDD Pacing in Patients with End-Stage Heart Failure", JACC 1998;32:1825-1831.

Lee et al., "Effect of implantable Defibrillators of Arrhythmic Events and Mortality in the Multicenter Unsustained Tachycardia Trial," Circulation. 2002; 106:233-238.

Linde et al., "Long-Term Benefits of Biventricular Pacing in Congestive Heart Failure: From the Multisite Stimulation in Cardiomyopathy (MUSTIC) Study", J Am Coll Cardiol 2002;40:111-118.

Miracle Trial Investigators, "Combined Cardiac Resynchronization and Implantable Cardioversion Defibrillation in Advanced Heart Failure: the Miracle ICD Trial," JAMA 2003;289:2685-2694.

Mirza et al, "Biatrial Pacing for Paroxysmal Atrial Fibrillation", J Am Coll Cardiol 2002;40:457-463.

Moss et al., "Prophylactic Implantation of a Defibrillator in Patients with Myocardial Infarction and Reduced Ejection Fraction," N Engl J Med. 2002; 346:877-933.

Niehaus et al., "Non-Contact Cardiac Stimulation with locused Ultrasound Pulses," PACE 2003: 26:1023.

Nielsen et al., "A Randomized Comparison of Atrial and Dual-Chambered Pacing in 177 Consecutive Patients With Sick Sinus Syndrome," J Am Coll Cardiol 2003;42:614-623.

Nolte et al., "Mechanically Induced Ventricular Extrasystoles in the Isolated Perfused Guinea-Pig Heart," Arzneim.-Forsch/Drug Research. 1987; 37(11): 1025-1029.

Peschar et al., "Left Ventricular Septal and Apex Pacing for Optimal Pump Function in Canine Hearts," J Am Coll Cardiol, 2003;41:1218-26.

Reiter et al.., "Effects of Mechano-Electrical Feedback: Potential Arrhythmogenic Influence in Patients With Congestive Heart Failure," Cardiovascular Research, 1996; 32:44-51.

Smailys et al., "Investigation of the Possibilities of cardiac Defibrillation by Ultrasound," Resuscitation, 1981; 9:233-242.

Sowton, "Clinical Results with the Tachylog Antitachycardia Pacemaker", PACE 1984; 7(Part II):1313-1317.

Tacker, Chapter 1: Fibrillation causes and criteria for defibrillation. In Defibrillation of the Heart. Tacker, WA, ed. Mosby-Year Book, Inc., St. Louis, Missouri, 1994, pp. 1-14.

The Antiarrhythmics Versus Implantable Defibrillators (AVID) Investigators, "A Comparison of Antiarrhythmic Drug Therapy with Implantable Defibrillators in Patients Resuscitated from Near Fatal Ventricular Arrhythmias," N Engl J Med ,1997;337: 1576-1583.

Valls-Bertault et al., "Adverse Events with Transvenous Left Ventricular Pacing in Patients with Severe Heart Failure: Early Experience from a Single Centre," Europace, 2001;3:60-63.

Warren et al., "Clinical Evaluation of Automatic Tachycardia Diagnosis by an Implanted Device", PACE 1986;9 (Part II):1079-1083.

* cited by examiner

IMPLANTABLE TRANSDUCER DEVICES

CROSS-REFERENCES TO RELATED APPLICATIONS

This application is a continuation of U.S. patent application Ser. No. 11/315,524, filed on Dec. 21, 2005, and claims the benefit of the following provisional applications: 60/639,027, filed on Dec. 21, 2004; 60/689,606, filed on Jun. 9, 2005; and 60/639,056, filed on Dec. 21, 2004. The full disclosures of each of these prior filings are incorporated herein by reference.

The subject matter of this application is related to that of the following commonly owned patent applications: Ser. No. 10/869,242; Ser. No. 10/869,776; and Ser. No. 10/869,705. The full disclosures of each of these prior filings are incorporated herein by reference but the benefit of the filing dates is not being claimed.

BACKGROUND OF THE INVENTION

1. Field of the Invention

The stimulation of cardiac tissue using an acoustic transducer, referred to as a controller-transmitter, and one or more implanted receiver-stimulator devices has recently been proposed by the inventors herein in the patent applications referred to above. The controller-transmitter produces an acoustic signal which is received by the receiver-stimulator, and the receiver-stimulator in turn generates an electrical signal which is delivered to cardiac or other tissue through coupled tissue electrodes. The controller-transmitter may be external, but will usually be implanted, requiring that the controller-transmitter have a reasonable size, similar to that of implantable pacemakers, and that the controller-transmitter be capable of operating from batteries for a lengthy period, typically three or more years. The relatively small size and relatively long operational period require that the receiver-stimulators efficiently utilize the acoustic energy from the controller-transmitters.

For those reasons, it would be desirable to provide implantable transducer devices which are able to efficiently receive acoustic energy from implanted or external acoustic transmitters. It would be particularly desirable if the transducers could operate in an isotropic or nearly isotropic fashion where they could efficiently receive acoustic energy from an acoustic transmitter regardless of the relative orientation between the transmitter and the implanted transducer. At least some of these objectives will be met by the inventions described hereinafter.

2. Description of the Background Art

The following patents and patent publications describe various implantable transducers capable of converting applied acoustic energy into an electrical output: U.S. Pat. Nos. 3,659,615; 3,735,756; 5,193,539; 6,654,638; 6,628,989; and 6,764,446; U.S. Patent Application Publications 2002/0077673; 2004/0172083; and 2004/0204744; and published German application DE 4330680.

BRIEF SUMMARY OF THE INVENTION

Systems and methods are provided for delivering electrical energy to body tissues for a variety of purposes. The energy will typically be delivered in order to stimulate cardiac tissue, for example in cardiac pacing for bradycardia, for termination of tachyarrhythmia, for bi-ventricular resynchronization therapy for heart failure, or the like. The systems and methods of the present invention, however, could be used in a variety of other applications, including applications for nerve stimulation, brain stimulation, voluntary muscle stimulation, gastric stimulation, bone growth stimulation, pain amelioration, and the like.

In a first aspect, the present invention provides an implantable receiver-stimulator device which is capable of receiving acoustic energy delivered from an acoustic source (physically separate from the receiver-stimulator device) and converting that acoustic energy to an electrical signal. The receiver-stimulator of the present invention will usually be very sensitive and will usually be able to receive and convert low levels of acoustic energy to produce electrical signals which are able to stimulate myocardial tissue. Typically, with devices of the present invention with cross sectional areas on the order of 3 mm$^2$, an acoustic wave having a pressure level in the range from 0.2 to 0.4 mega Pascals (an intensity level of 1.3 to 5.6 W/cm$^2$), can be converted to electrical signals in the range from 1.0 to 2.0 Volts. Thus, the devices of the present invention will usually be very efficient and capable of converting a large portion of the received acoustic energy into electrical energy, typically with a conversion efficiency of at least 25%, often being at least 50%. In addition to such high sensitivity and efficiency, the implantable receiver-stimulators of the present invention are also capable of functioning at least substantially isotropically. That is, the device sensitivity will be isotropic. By "isotropic," it is meant that the receiver-stimulator will have a transducer assembly capable of receiving acoustic energy in a manner which is substantially insensitive to the relative orientation of the device to the acoustic source. The electric signal produced by the receiver-stimulator device in response to incident acoustic energy will vary by no more than ±6 dB as the orientation of the device varies relative to the acoustic source, often varying by no more than ±3 dB, preferably varying by no more than ±1 dB.

In a first specific embodiment, an implantable receiver-stimulator comprises a transducer assembly, typically being capable of isotropic operation as noted above, which receives acoustic energy from an acoustic source and which produces an electrical signal in response to the acoustic energy. The device further comprises demodulator circuitry which receives the electrical signal and which produces a biologically stimulating electrical output, e.g., suitable for cardiac pacing, nerve stimulation, brain stimulation, voluntary muscle stimulation, pain amelioration, or the like. The device will further include at least two tissue-contacting electrodes which are coupled to the demodulator circuitry to receive the stimulating electrical output and deliver said output to the tissue. Either or both of the electrodes may be mounted directly on the device, in some instances forming a portion of the device casing, or may alternatively be connected to the device by wires, cables, or the like, for placement.

The transducer assembly may comprise a cylindrical piezoelectric transducer having a pair of electrodes formed over opposed surfaces thereof. The incident acoustic energy will cause the piezoelectric transducer to vibrate and generate electrical charge which is collected by the electrodes and available for delivery to the demodulator circuitry. In a first exemplary embodiment, the piezoelectric transducer may be composed of a polycrystalline ceramic piezoelectric material. When the ceramic piezoelectric material is formed in the shape of a tube, the opposed electrodes may typically be formed over the outer and inner cylindrical surfaces of the transducer although electrodes over the opposing flat end surfaces may also be used.

In a preferred exemplary embodiment, however, the piezoelectric transducer will be composed of a single crystal material, typically being cut in the <001> orientation. A preferred single crystal material comprises PMN-xPT material, where x is in the range from 5% to 50% by weight. Other single crystal materials may be of the composition PZN-xPT, or Relaxor-PT materials. When the piezoelectric transducer is composed of a single crystal, the opposed electrodes are preferably formed over the opposed flat end surfaces of the cylinder, not the cylindrical surfaces. Alternatively, for alternate crystal planes, electrodes formed on cylindrical surfaces or cylindrical surfaces on sectioned and composite crystal assemblies, may be preferred.

In a still further embodiment of the implantable receiver-stimulator of the present invention, the transducer assembly comprises a plurality of individual transducer elements. The demodulator circuitry similarly comprises a plurality of individual demodulator circuits, and each of the transducer elements is attached to one of the individual demodulator circuits. The transducer elements themselves will typically have a maximum dimension which is approximately one-half wavelength of the expected acoustic transmission, but the cumulative lateral dimensions of the individual transducer elements will preferably be much greater than a single wavelength. On the output of the demodulator circuitry there will be provisions for summing the electrical signals from each of the individual demodulator circuits to produce the biologically stimulating electrical output. Electrical signals may be summed in parallel, in series, or in a series-parallel combination.

In a second aspect of the present invention, methods for delivering energy to an implanted receiver-stimulator comprise implanting a receiver-stimulator, typically formed as an assembly having a transducer or transducers, being substantially isotropic as described above in connection with the devices of the present invention. Acoustic energy is directed to the implanted receiver-stimulator assembly from an acoustic source, which may be implanted or located externally, and the transducers produce electrical signals which vary by no more than ±6 dB as the orientation of the transducers vary relative to that of the acoustic source. The electrical signal is demodulated to produce a biologically stimulating electrical output, and the electrical output is delivered to tissue. The acoustic energy may be delivered to the receiver-stimulator from an external source, but will preferably be delivered from an implanted acoustic source. The electrical output flowing between stimulating electrodes which are in contact with tissue may possess specific characteristics of voltage, current, waveform, and the like. These electrical characteristics will be selected to stimulate the target cardiac tissue, nerve tissue, brain tissue, voluntary muscle tissue, bone tissue, or the like.

DETAILED DESCRIPTION OF THE INVENTION

Figure 1:
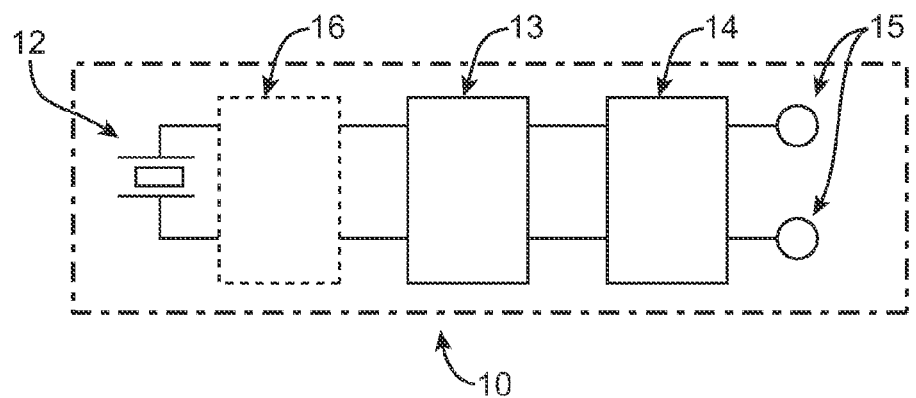
FIG. 1 is a block diagram illustrating a receiver-stimulator constructed in accordance with the principles of the present invention.

As illustrated in FIG. 1, an exemplary receiver-stimulator 10 constructed in accordance with the principles of the present invention comprises a transducer assembly 12, demodulator circuitry including a rectifier circuit 13 and a filter circuit 14, and tissue-contacting electrodes 15. Optionally, impedance matching circuit 16 may be provided to match the output of the transducer assembly with the electrical impedance presented by the rectifier/filter circuits and the tissue contacted by the electrodes. The present invention provides certain specific designs for the transducer assembly 12 and for assemblies of transducers which in turn provide a highly isotropic receiver-stimulator operation such that the output of the transducer or transducers is highly independent of the orientation of the transducer or transducers relative to an acoustic source.

Figure 2:
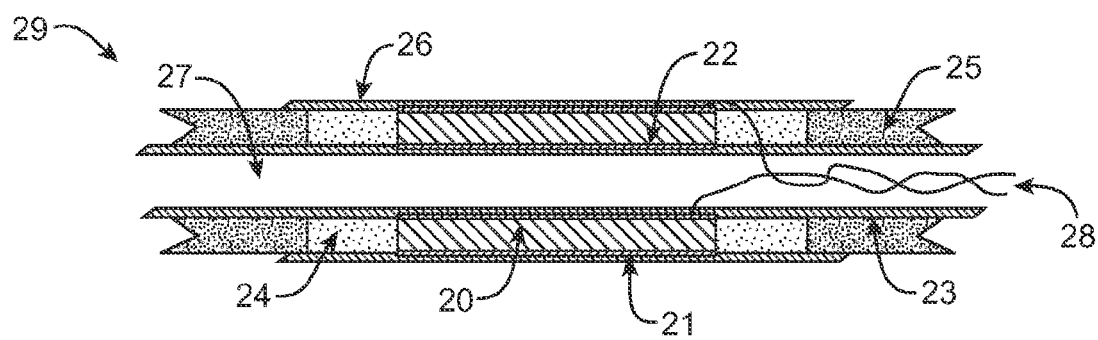
FIG. 2 illustrates a first exemplary transducer design of a type useful in the receiver-stimulators of the present invention.
Figure 4:
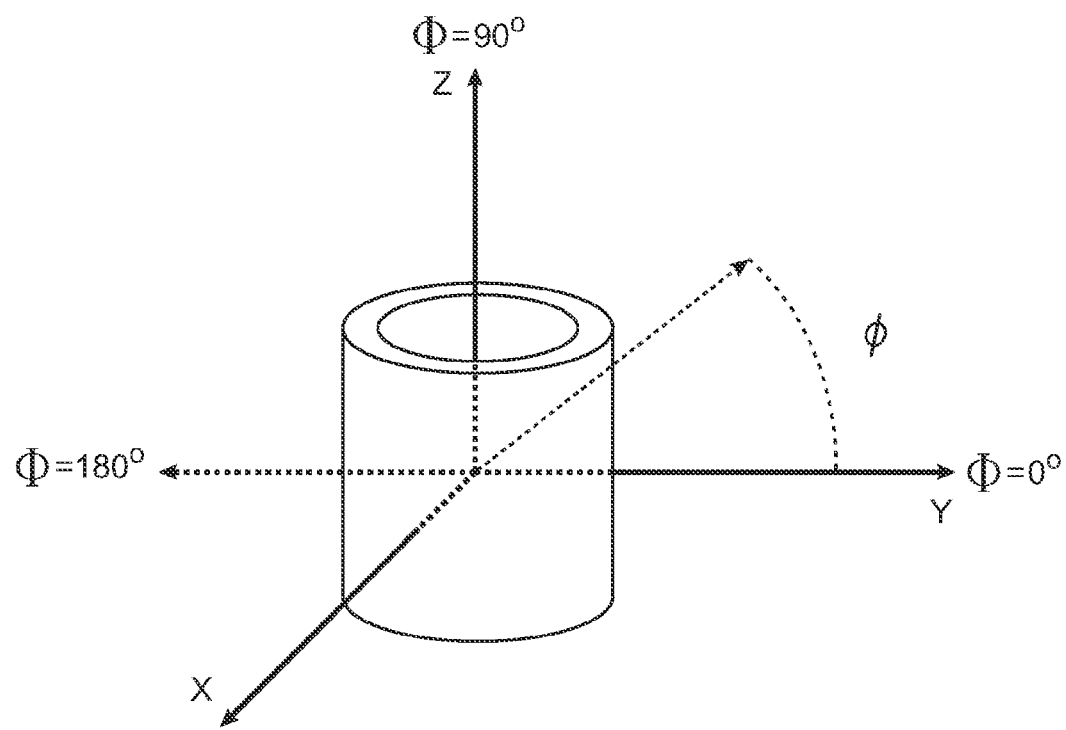
FIG. 4 is a schematic illustration of the elevation angle definition for beam profile measurement.

A first nearly isotropic transducer assembly 29 useful in the present invention is illustrated in FIG. 2. The transducer assembly 29 generally comprises a cylindrical polycrystalline piezoelectric tube 20 with an outer cylindrical electrode 21 and an inner cylindrical electrode 22. Typically the ceramic may be mounted on a thin walled tube 23 of polyamide or other suitable material, with or without an epoxy bond between the inner wall of the ceramic and the outer wall of the tube. Both flat faces of the ceramic may have an acoustic absorber 24 between the ceramic and before the start of the structural body 25. All internal surfaces are typically bonded with low viscosity epoxy. The outer surface of the assembly is typically coated with a low viscosity epoxy under a thin walled shrink tube 26. Prior to assembly, electrical leads 28 are soldered to the inner and outer electrodes, and passed through the hollow inner volume 27 of the inner tube. Optionally, other circuit components as shown in FIG. 1 may also be positioned in the hollow inner volume 27. Devices of this type can provide near isotropic sensitivity, typically on the order of 6-12 dB down, in the elevation angle along the cylindrical axis as compared to the sensitivity normal to the cylindrical axis, where the elevation angle with respect to the cylindrical axis is depicted in FIG. 4.

Figure 3:
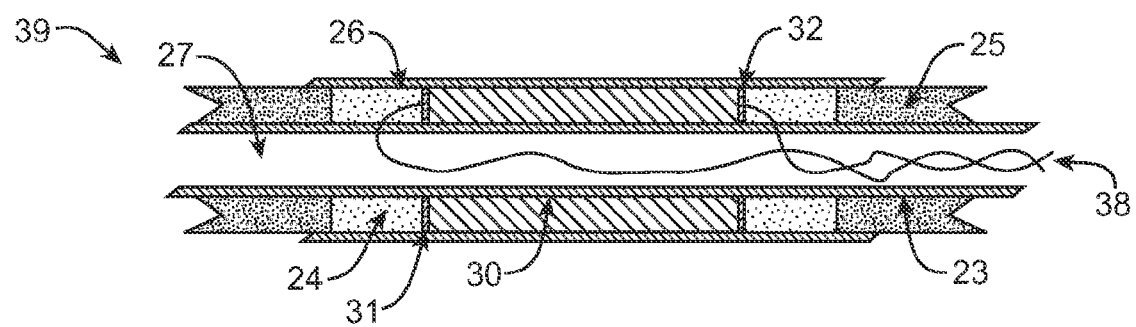
FIG. 3 illustrates a second exemplary transducer design of the type useful in the receiver-stimulators of the present invention, particularly being useful with single crystal transducers.

While the transducer assembly 29 of FIG. 2 provides a high degree of isotropic sensitivity, it would be desirable to provide transducer assemblies which operate even more isotropically. Referring to FIG. 3, the use of single crystal piezoelectric materials can provide further enhancement. A single crystal device 39 would be fabricated in a similar manner to the polycrystalline ceramic device, with the exception that the electrodes 31 and 32 of the single crystal piezoelectric would be on the flat faces of the cylinder 30 which is a single crystal material cut in the <001> orientation, and wired accordingly with leads 28. Standard crystallographic terms are used here to define crystal axes. The Miller indices (hkl) define the orientation of a plane with respect to the crystal axes. A separate axis perpendicular to the plane (hkl) is defined by the term <hkl>. Therefore, a (001) plane would be parallel to the xy crystal plane and perpendicular to the crystal z axis. The <001> axis is thus parallel to the crystal z axis.

Devices of the type depicted in FIG. 3 have been fabricated with single crystal component sizes virtually identical to the ceramic components. As detailed below, there are similarities in performance such as beam profiles. Most significantly, the single crystals have superior isotropic sensitivity, especially at a low frequency resonance which is not achieved by the higher frequency resonance of the ceramic piezoelectrics.

Figure 5:
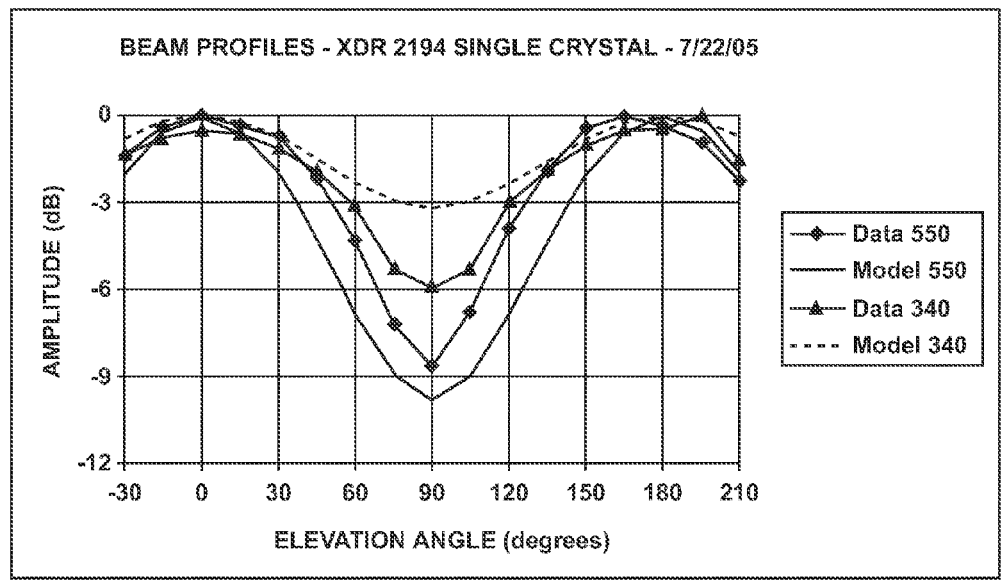
FIGS. 5 and 6 illustrate the elevation angle beam profiles for a single crystal transducer and a polycrystalline ceramic transducer.
Figure 6:
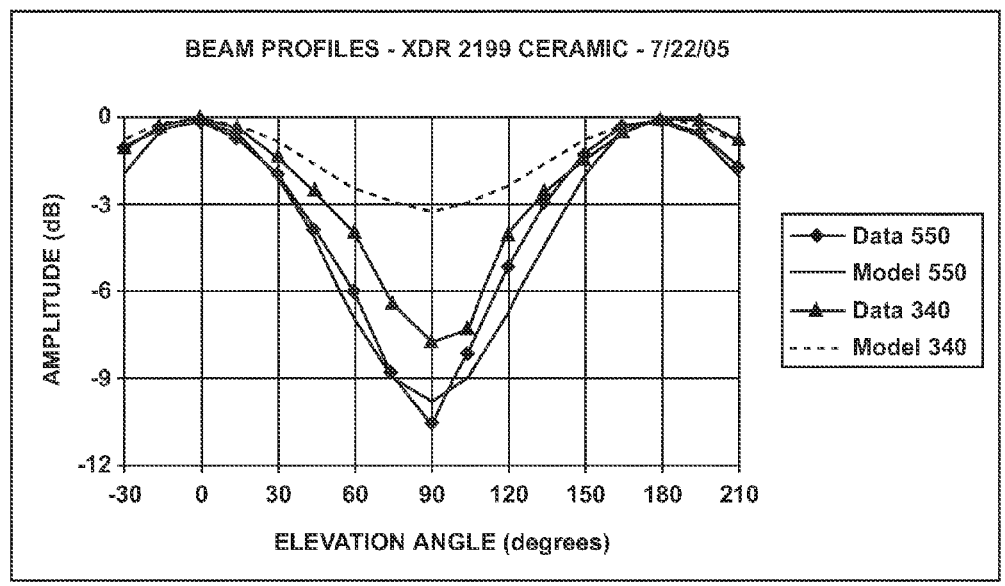

FIGS. 5 and 6 depict measured and model data for beam profiles at 340 kHz and 550 kHz of representative devices. The single crystal device profiles are depicted in FIG. 5 and the ceramic device profiles are depicted FIG. 6. For these profiles, the beam angle is defined as the elevation angle as depicted in FIG. 4. An elevation angle of 0 degrees corresponds to an incident beam normal to the cylindrical axis of the device, 90 degrees parallel to the cylindrical axis, and 180 degrees normal to the cylindrical axis, but in the opposite direction from 0 degrees. Due to symmetry, in the absence of gross fabrication defects, these devices will usually have sensitivity fluctuations of less than 1 dB in azimuth, around the cylindrical axis of the piezoelectric tube. With respect to the elevation angle, a perfectly isotropic device would have a flat response from 0 to 90 to 180 degrees. Further, at lower frequencies both devices exhibit less anisotropy than predicted by diffraction theory. However, the variation in anisotropy remains inconsistent with a simple diffraction model based on device size and frequency. Acoustic coupling through structural components of the test articles are assumed responsible for this discrepancy.

With respect to sensitivity, Table 1 below summarizes device sensitivity in a plane normal to the cylindrical axes of the devices. The devices were exposed to long bursts of ultrasound, in the general range of 340 kHz and 600 kHz. With no electrical load on the devices, the generated peak-to-peak voltage was measured by a high input impedance digital oscilloscope, with the results tabulated below with respect to the ultrasound field strength in MI (Mechanical Index, defined as rarefactional pressure in mega Pascals divided by the square root of the frequency in mega Hertz). Subsequently, in each test, the devices were electrically loaded with a 500 ohm resistor, with the results next tabulated below with respect to field strength. The electrical impedance of 500 ohms was used and was representative of the impedance between electrodes in contact with various human tissue types. And lastly, the devices were near optimally impedance matched with a transformer, connected to a full wave rectifier with a 0.1 micro Farad capacitor, and loaded with 500 ohms. The peak amplitude of the resulting DC (direct current) voltage envelope with respect to the field strength is reported below.

TABLE 1

| Device s/n | Type | Frequency (kHz) | Unloaded Vac/MI (Vpp) | 500 Ω Load Vac/MI (Vpp) | Det/Fil Vdc/MI (Vop) |
|---|---|---|---|---|---|
| 2199 | Ceramic | 550 | 8.90 | 5.40 | 2.05 |
| 2199 | Ceramic | 340 | 4.28 | 2.73 | 0.65 |
| 2216A | Crystal | 570 | 30.4 | 8.53 | 4.06 |
| 2216A | Crystal | 340 | 102.0 | 16.8 | 8.10 |

TABLE 1-continued

| Device s/n | Type | Frequency (kHz) | Unloaded Vac/MI (Vpp) | 500 Ω Load Vac/MI (Vpp) | Det/Fil Vdc/MI (Vop) |
|---|---|---|---|---|---|
| 2195 | Ceramic | 600 | 17.0 | 10.9 | 2.76 |
| 2195 | Ceramic | 340 | 3.70 | 1.97 | 0.41 |

In the above Table, device 2199 was a PZT-5H ceramic tube, 0.070 inches long, 0.070 inches in outside diameter, and 0.045 inches on inner diameter. The tube was polarized with electrodes on the inner and outer cylindrical surface. Device 2216A was a PMN-32% PT single crystal tube, with the same dimensions as device 2199. However, the device was cut from a plate perpendicular to the <001> crystal orientation axis. The electrodes were on the flat faces with polarization between the electrodes. Device 2195 was a ceramic tube in all aspects the same as device 2199, with the exception of a 0.040 inch length.

In an open circuit mode, the single crystal devices are vastly superior to the ceramic devices. However, this represents an unrealistic situation in that sufficient current needs to be derived from the devices to stimulate tissue. While the single crystal materials still enjoy a substantial advantage when loaded with a representative tissue impedance, the performance gap has lessened. And lastly, when driving impedance matching, rectifier, filter, and representative tissue loaded circuits, there was still a good performance gap, but with slight variations.

Figure 7:
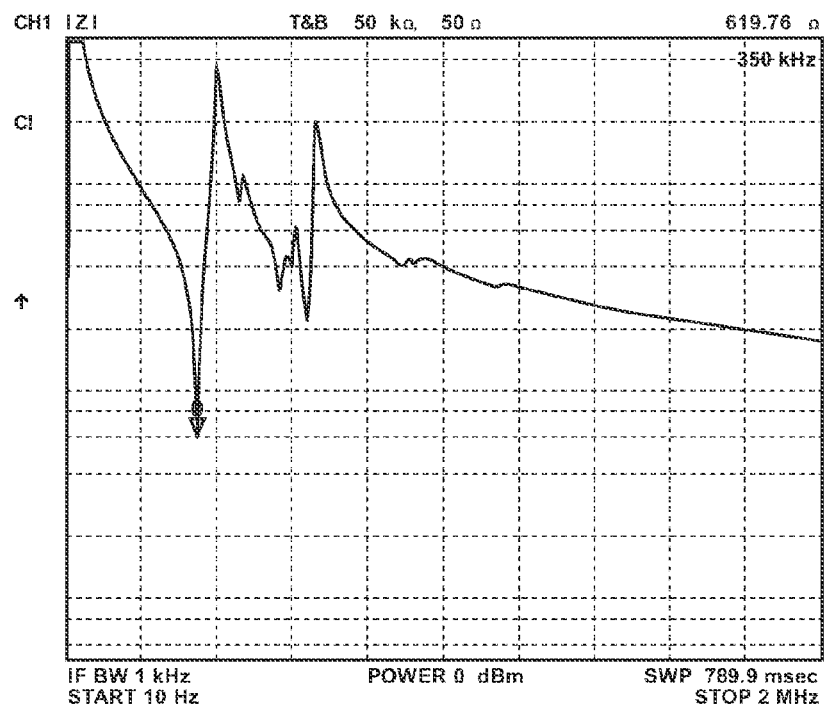
FIGS. 7-9 are impedance plots for different transducer materials.
Figure 8:
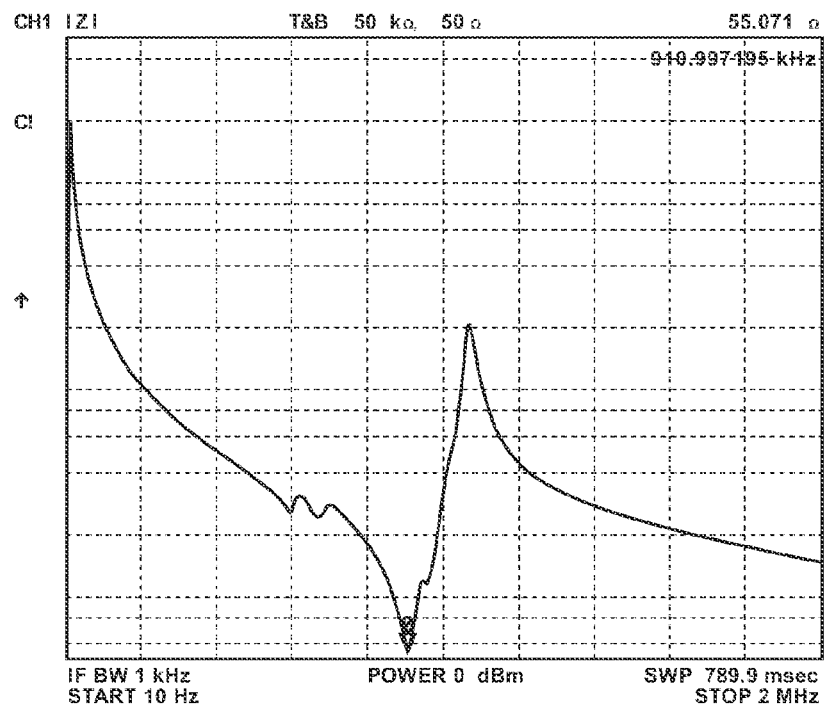
Figure 9:
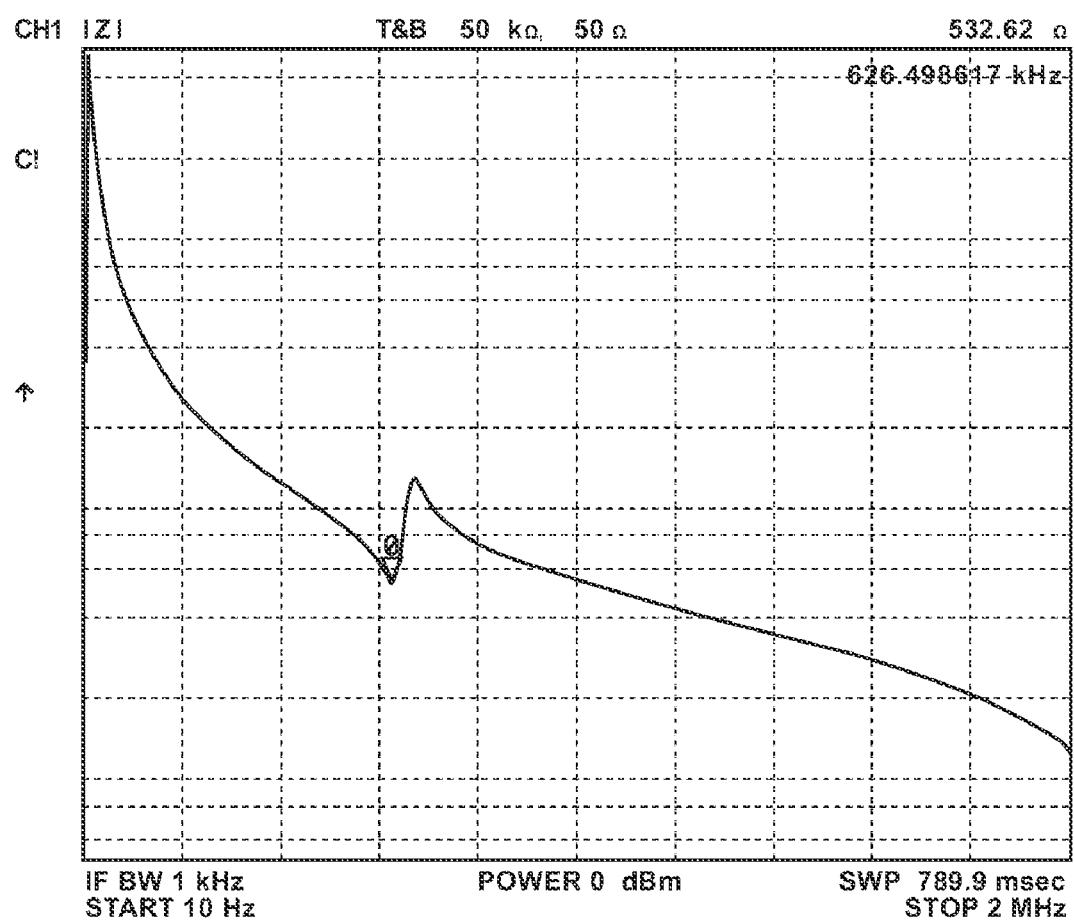

The primary reason for the excellent performance of the single crystal material was the low frequency constant which results in a resonance at approximately 340 kHz, as seen in FIG. 7. For the same sized piece of material, there exists a small resonance in the ceramic at approximately 600 kHz as seen in FIG. 8, thus slightly enhanced relative to the performance of the ceramic at 550 kHz. A much stronger resonance exists at approximately 900 kHz. This resonance unfortunately cannot be used as the wavelength thus becomes smaller than the device, predisposing the device to yet greater elevation angle anisotropy. Interestingly, in device 2195, with a length half that of 2199, the length mode resonance was pulled down to approximately 600 kHz as seen in FIG. 9, and thus the slightly better performance of the shorter device at 600 kHz was observed.

In comparing the performance of the single crystal at its resonance of 340 kHz with the ceramics at their lowest frequency resonances at 550 to 600 kHz, the single crystal device was still on average more than 10 dB more sensitive, fully loaded, than the ceramic devices. Comparing the single crystal at its off resonance frequency with the ceramics at their off resonance frequencies, the single crystal device was more than 17 dB more sensitive. The single crystal material was thus seen to offer significant improvement over the ceramic material as a source of electrical energy in an acoustic field for the tissue stimulator.

Figure 15A:
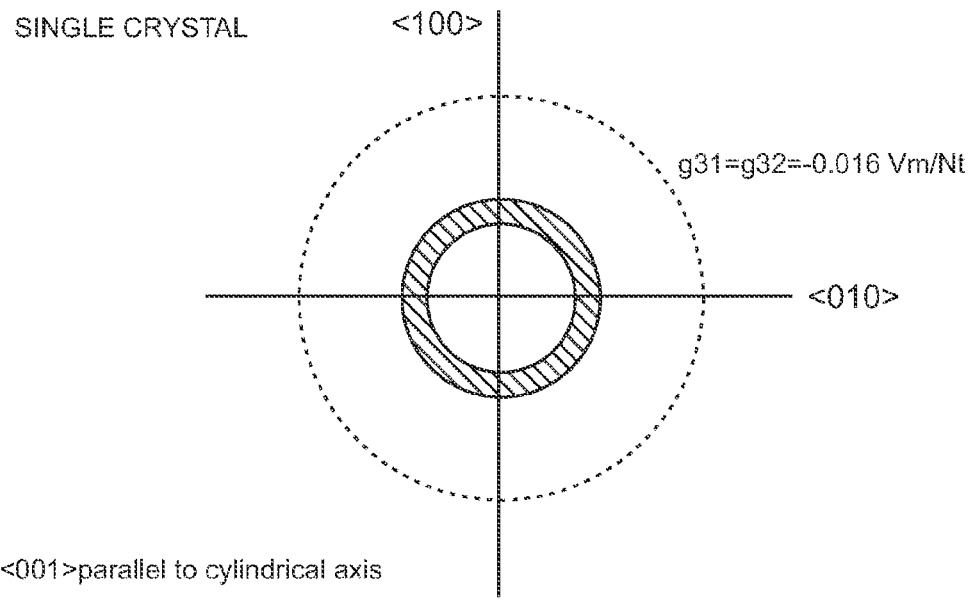
FIGS. 15A-15d illustrate various single crystal orientations and respective sensitivity profiles of transducer in the present invention.
Figure 15B:
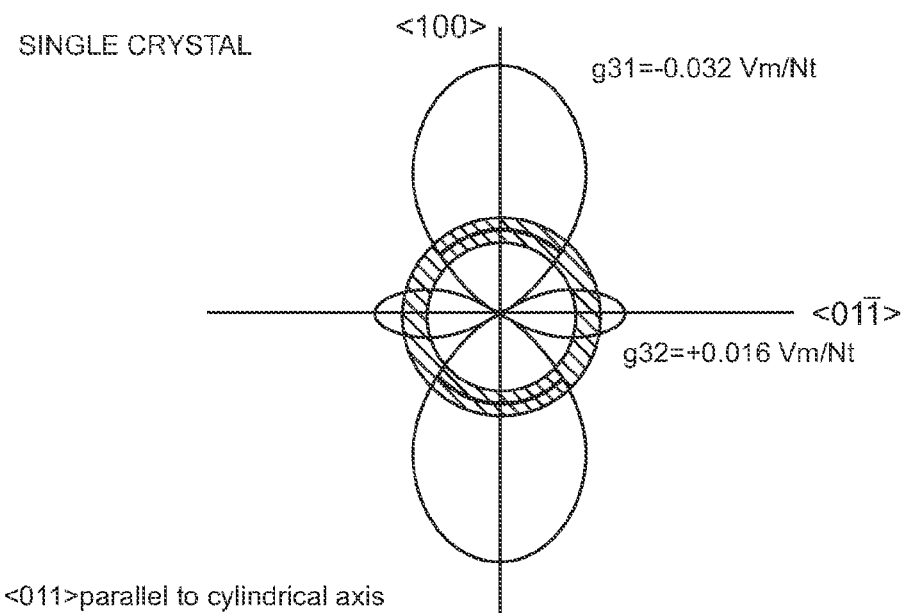
Figure 15C:
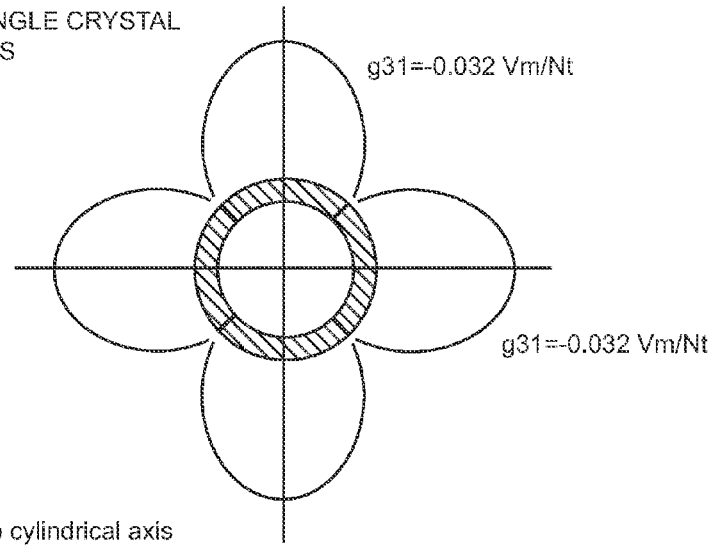
Figure 15D:
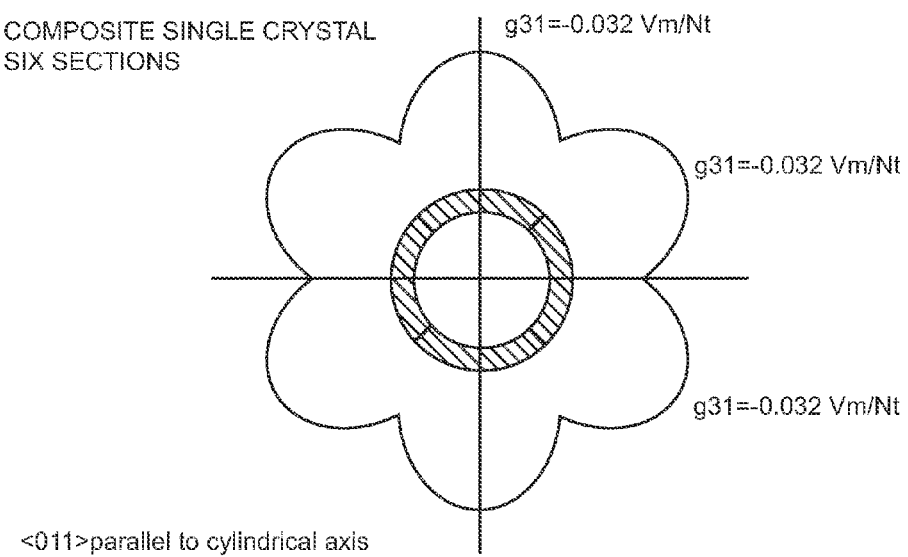

The present invention has detailed the implementation of single crystal piezoelectric tubes cut in the <001> orientation for use in implantable receiver-stimulator devices, where the sensitivity normal to the crystal axis is circumferentially uniform in all directions, as depicted in FIG. 15A by the dashed line around the tube cross sectional view. Multiple different orientation planes of single crystals also have potential utility. One such possible configuration would utilize the properties of the single crystal tube cut in the <011> plane, where the lateral sensitivity has a crossed dipole shape, with an amplitude in the <100> direction higher by a factor of approximately two than the single crystals discussed above, but with an orthogonal sensitivity being of reverse polarity and less amplitude, as depicted in FIG. 15B. If this crystal were to be directly implemented, the reverse polarity sensitivity would detract from the stronger orthogonal dipole lobes, and yield a device with perhaps less sensitivity than the devices as described above. However, if quadrants of the single crystal comprising the higher sensitivity dipole lobes (as highlighted by the arcs in FIG. 15B) were to be cut out, and four quadrants of this high sensitivity material reassembled as depicted in FIG. 15C, the net effect would be a single crystal tube with high sensitivity in all four quadrants, and net greatly increased sensitivity. Since the original tubular shape has been maintained, all mechanical resonances within the device remain the same. Alternatively, the cut sections with favorable crystal orientation may be smaller, 60 degrees of arc instead of 90 degrees of arc, and reassembled, as depicted in FIG. 15D, for yet higher sensitivity. Since the anticipated operating wavelength is larger by approximately a factor of two than the physical size of the reassembled device, the sensitivity will be averaged over the surface of the device.

A further embodiment of the implantable receiver-stimulators of the present invention utilizes a transducer assembly which includes multiple transducer elements at least some of which have a size (equal to or less than one-half wavelength) selected to enhance the isotropic nature of the individual elements. Generally if the piezoelectric transducer size exceeds one half wavelength of the acoustic signal, directional variations in sensitivity will begin to dominate performance, whereas with device sizes less than one half wavelength, device sensitivity approaches isotropy, being almost uniform in all directions. Hydrophones, which are devices to sample acoustic fields, typically have upper operational limits corresponding to a sensor size of one half wavelength. Larger sizes would be preferred for hydrophone elements as the output is directly proportional to the cross sectional area of the device. Thus, for the receiver-stimulator, multiple elements are added specifically to increase the cross sectional area of the device to increase sensitivity. The implantable devices must have near isotropic responses, as the orientation of a device with respect to the acoustic excitation field may not coincide with the orientation of the device as it is implanted in the tissue which requires stimulation.

Figure 10:
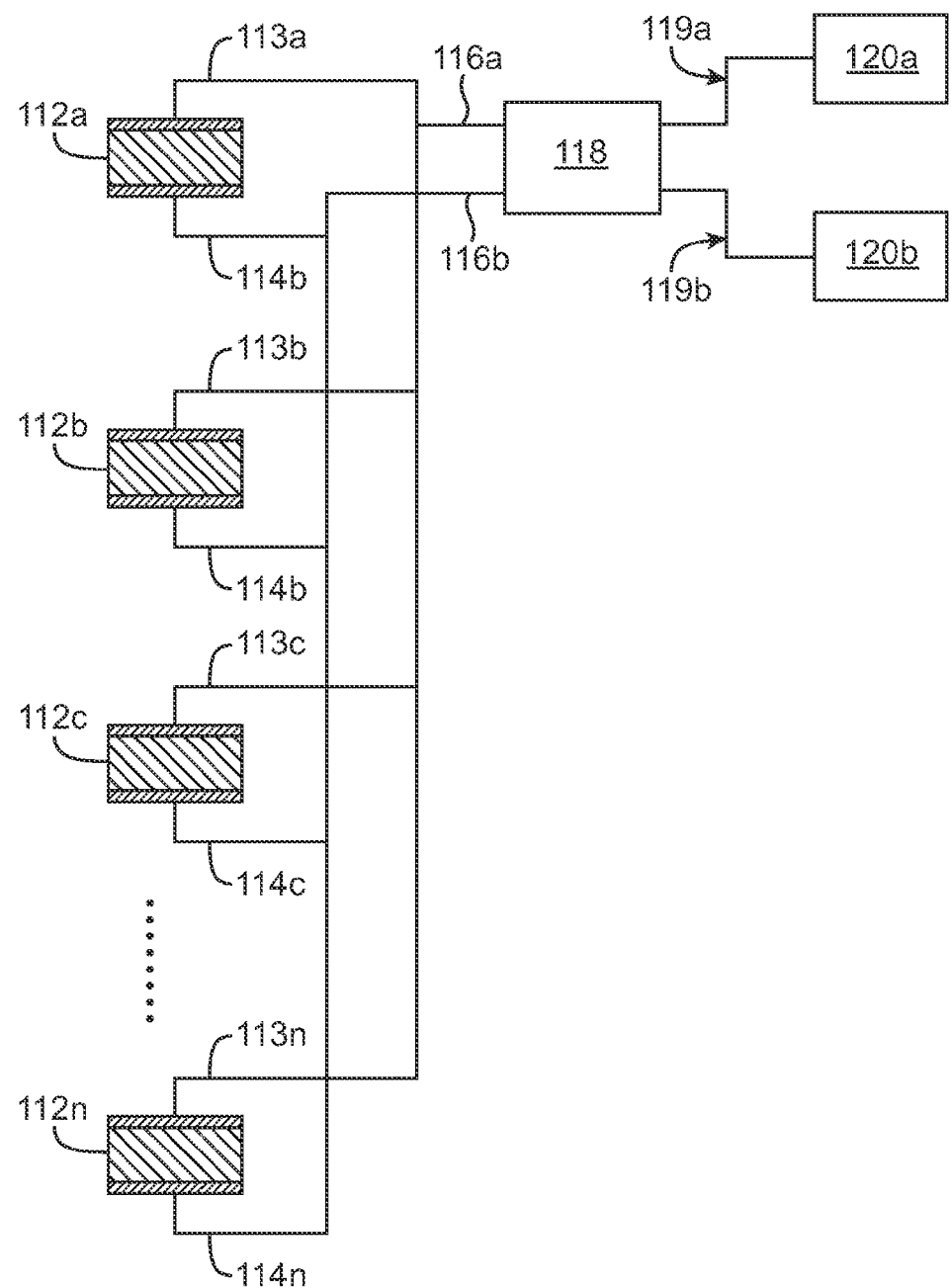
FIG. 10 is an embodiment of transducer assemblies employing multiple transducer elements

As depicted in FIG. 10, a transducer assembly featuring multiple elements 112a, 112b, 112c, 112n and output leads 113a, 114a, 113b, 114b, 113n, 114n are wired in parallel to a single pair of connecting leads 116a and 116b to a single detector/filter circuit 118, which passes the combined signal to tissue contact stimulation electrodes 120a and 120b, via leads 119a and 119b. This technique, however, while offering more ceramic volume to achieve a greater power output, is subject to the constructive or destructive interference of signals into the detector/filter 118 from each of the individual elements due to the different arrival times of the signals from each element. It would be difficult to position the set of individual elements in such a manner as to assure only constructive interference of the individual signals. This configuration offers high sensitivity only when the phase of the incident acoustic signal is identical at each element and thus is not a preferred embodiment of the present invention.

Figure 11:
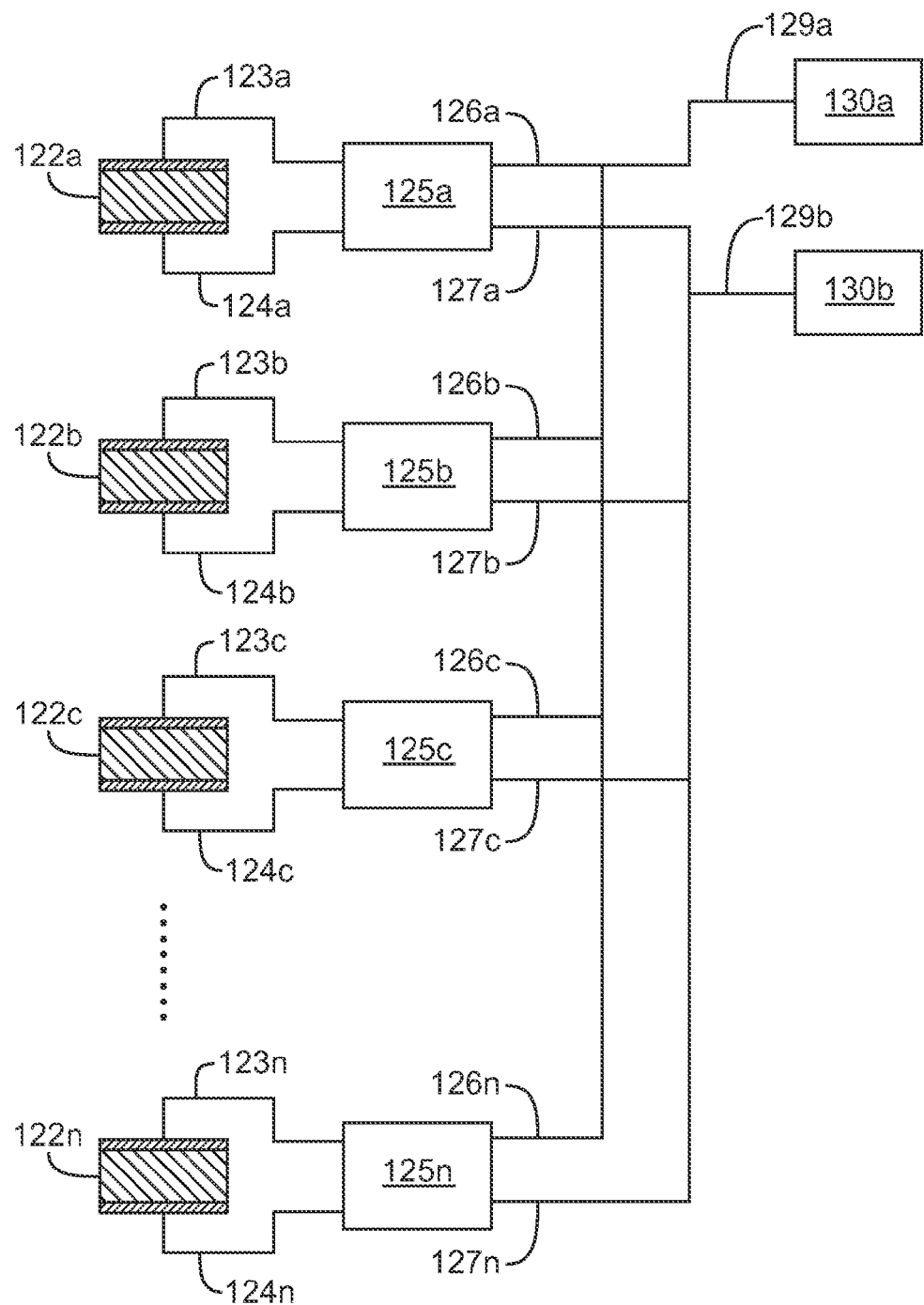
FIGS. 11-12 are two embodiments of transducer assemblies employing multiple transducer elements in accordance with the principles of the present invention.

In order to overcome this deficit and yet to use multiple elements for greater output power, and to reduce or eliminate constructive and destructive interference between the elements, a separate detector/filter for each element is provided. The combination of a single transducer element and a single detector/filter may be referred to as a channel. As depicted in FIG. 11, individual elements 122a, 122b, 122c, 122n drive their own respective detector/filters 125a, 125b, 125c, 125n via their leads 123a, 124a, 123b, 124b, 123n, 124n. The output leads 126a, 127a, 126b, 127b, 126n, 127n of the detector/filters are wired in parallel via leads 129a and 129b and are thence connected directly to the stimulation electrodes 130a and 130b. In this manner, the current delivery of the device (assuming the elements are all the same and receive the same acoustic signal) is multiplied by the number n of individual channels within the device.

Figure 12:
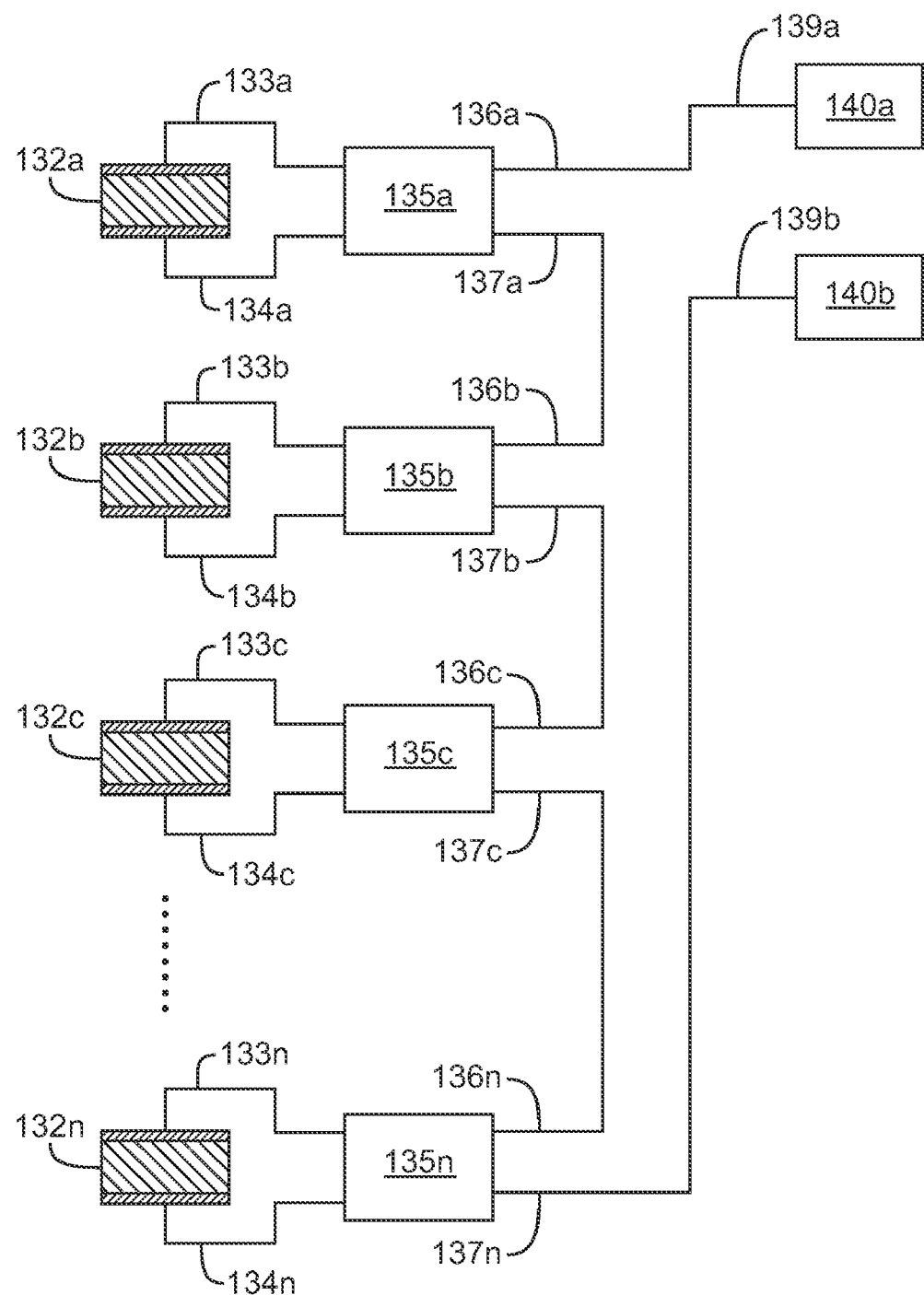

Alternatively, as depicted in FIG. 12, the outputs of the individual detector/filters can be wired in series, with output leads 139a and 139b passing directly to the tissue stimulation electrodes 140a and 140b, while intermediate leads such as 137a and 136b between channels are connected. In this manner, the voltage delivery of the device (assuming the elements are all the same and receive the same acoustic signal) is multiplied by the number n of individual channels within the device.

Further, it is also possible to combine series and parallel connections on the outputs of the individual channels to achieve at least partially specific impedance matching between the individual piezoelectric elements and a target tissue mass.

Figure 13:
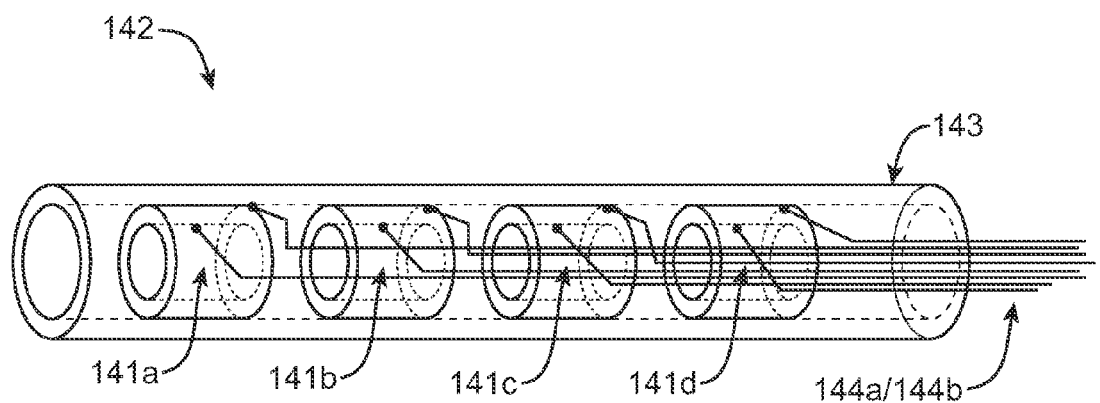
FIG. 13 illustrates an exemplary construction for a transducer assembly having multiple individual transducer elements.

To demonstrate this concept, a multi-element section 142 was fabricated as depicted in FIG. 13, comprising four individual cylindrical tube transducer elements 141a to 141d, which were epoxy bonded to the inside wall of thin walled polyimide tubing 143. Transducer electrode lead wires 144a to 144h were fed to one end of the tubing. There was no fluid path to the hollow air-filled inside of the polyimide tube. The individual transducer elements had an outer diameter of approximately 0.6 wavelengths and a length of approximately 0.8 wavelengths, with a gap between elements of approximately 0.6 wavelengths at 500 kHz. In this prototype implementation, the detector/filter circuits were voltage doublers, as described in a co-pending application.

Figure 14A:
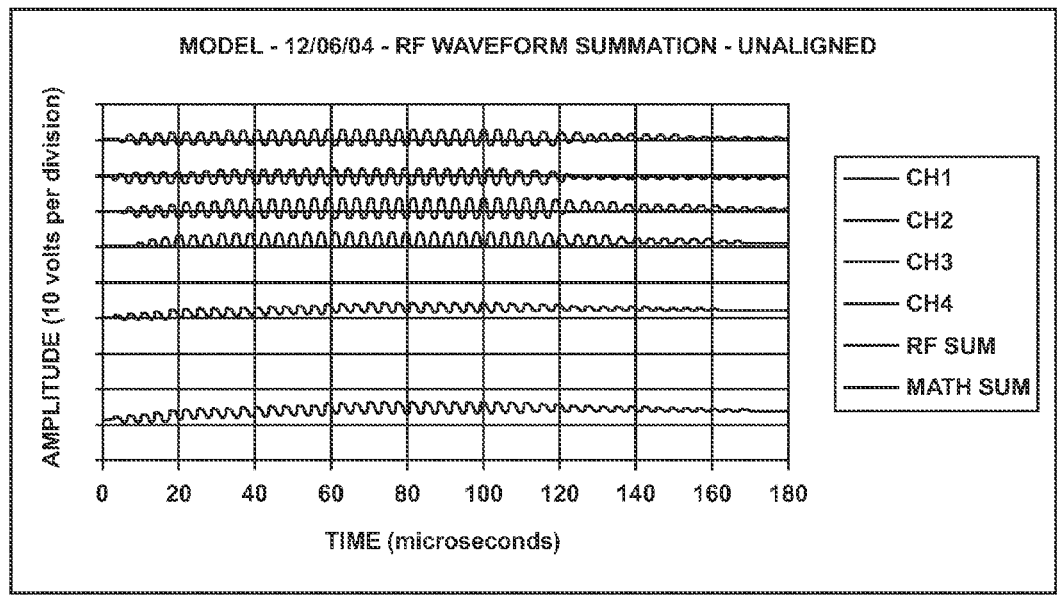
FIGS. 14A-14I show exemplary waveform summation plots produced by the multiple element transducer assemblies of the present invention.
Figure 14B:
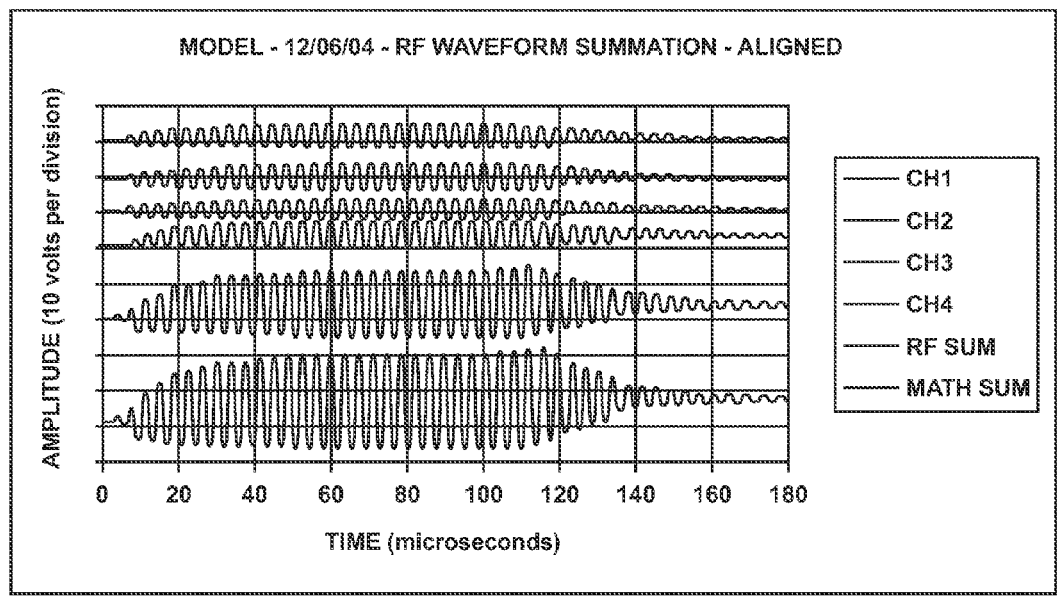

In FIGS. 14A and 14B the traces from top to bottom follow the top to bottom order of the index to the right of the chart. FIG. 14A depicts the output voltage from each of the four elements (top four traces) when the device was oriented askew with respect to an ultrasound beam. Because of the random phase variations among the elements, a series connection (RF SUM) resulted in a net signal weaker than that from any element on its own. Indeed, if the outputs of the individual elements were to be mathematically summed (MATH SUM), the waveform is virtually identical to that of the RF SUM. Even though each individual element may have had a near isotropic response, destructive interference of the series-connected individual element signals has given a diminished output. The slight variations in the amplitudes of the four elements is due to slight fabrication variations and possible interaction of the acoustic beam between the elements.

FIG. 14B depicts a more ideal case, where the four elements are aligned virtually perpendicular to the ultrasonic beam. Since the size of the individual elements was slightly greater then the nominal half wavelength rule recited above, there is a slightly greater output of the individual element (top four traces) in this case, than in the previous "random alignment" angled case. In the same manner as above, the RF SUM represents the hardware wired combination of devices compared to the mathematical combination, MATH SUM. Note however that the RF SUM is slightly lower in amplitude than the MATH SUM. During the measurements, the individual elements were connected to individual open ended detector/filter circuits which presented a different electrical load as when the elements where wired in series and connected to a single open ended detector/filter circuit. Note further that in stark contrast to FIG. 14A, the phases of channel 1 to channel 4 are precisely aligned.

Figure 14C:
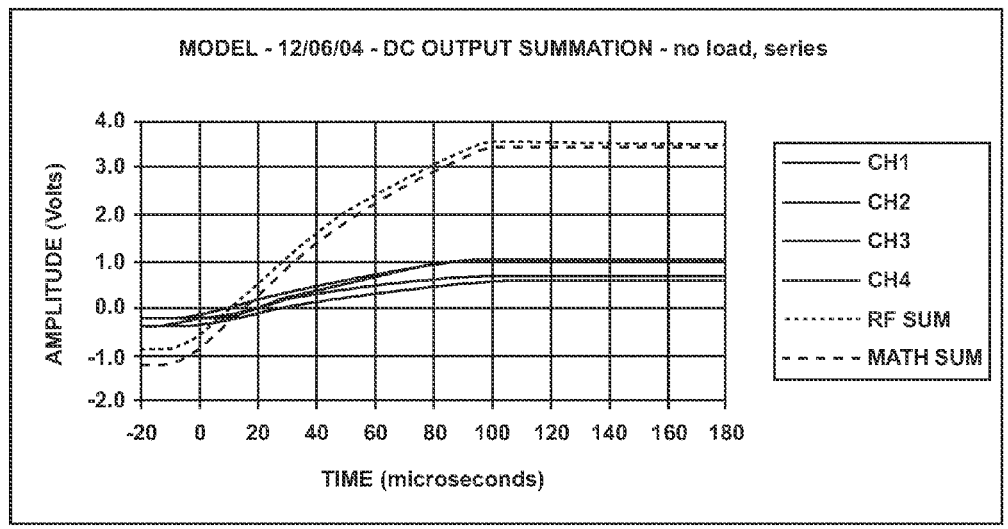
Figure 14D:
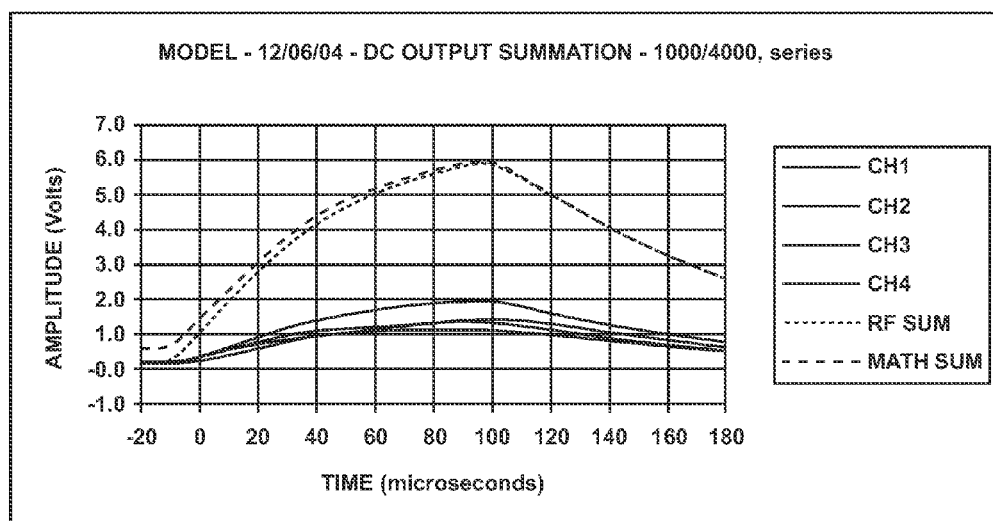

When looking at the output of the detector/filter circuit under a no load condition, the output voltage falls off very slowly as compared to the voltage rise due to the input signal from the transducer element. This is seen in the lower four traces of FIG. 14C for the four channels (transducer element and detector/filter), where from approximately −5 microseconds to 100 microseconds the individual transducer elements are exposed to an ultrasonic field. In this case, and for all measurements of the remaining figures, the orientation of the four transducers with respect to the acoustic beam is skewed, causing random phases for the output of the individual transducer elements, as was the case for FIG. 14A. In FIGS. 14C and 14D the top two traces represent the hardware summation of the DC output of the detector/filters, and the mathematical sum of the individual outputs. Note that the actual hardwired summation is virtually identical to the mathematical sum of the individual channels. This is in stark contrast to the hardwired case of FIG. 14A, where hardwired summation was performed on the output of the individual transducer elements with a single detector/filter.

Figure 14E:
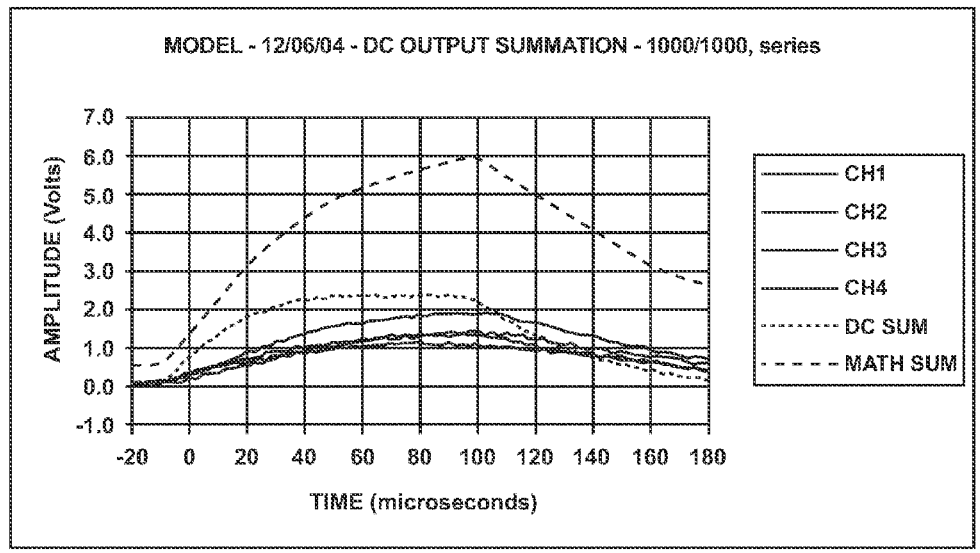

FIG. 14D represents the same conditions as FIG. 14C, except the outputs of the individual channels, comprising the individual transducer elements and their respective detector/filter circuits, were loaded with 1000 ohms, and the hardwired post detector summation was loaded with 4000 ohms. With 4000 ohms on the summed output, the current delivery from each channel was the same as in the unsummed state. Indeed, FIG. 14E represents the same scenario wherein the hardwired output is loaded with 1000 ohms, which placed a factor of four higher current demand on each of the four channels, and which consequently resulted in a significantly lower amplitude DC SUM since the individual transducer elements were unable to meet the demand. Further, the waveform of the summed output has become markedly flattened, clearly demonstrating the current threshold of the elements. Note also that in this case of resistive loading on the individual channels and on the summed outputs, while the rise time of the detector/filter circuit is the same as before, the fall time is reduced, due to the drain of charge off the filter capacitors.

Figure 14F:
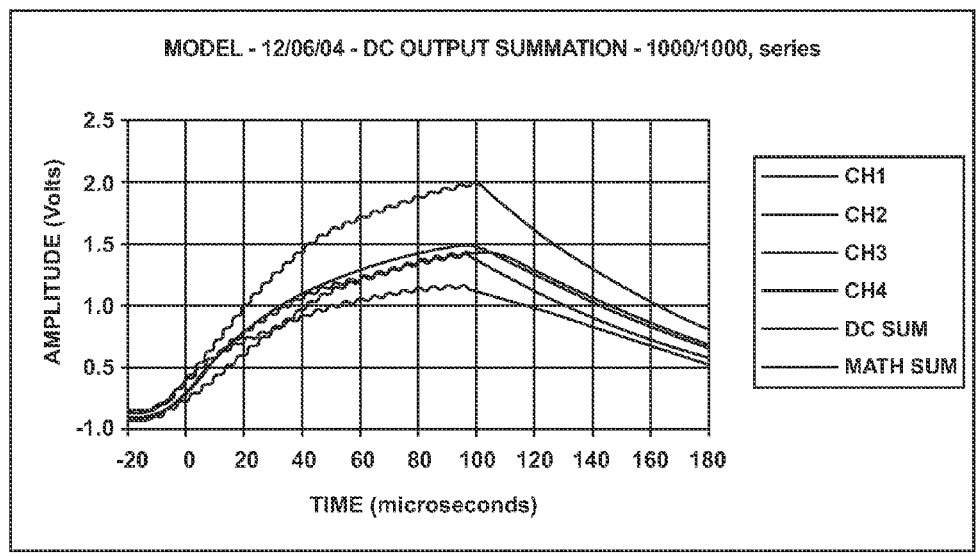
Figure 14G:
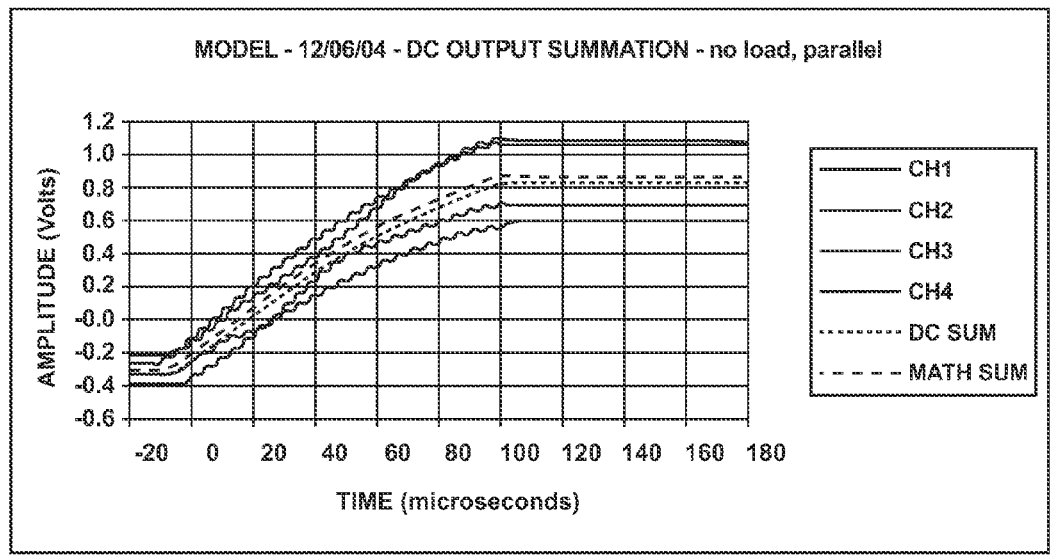

FIGS. 14G and 14F represent the same conditions as FIGS. 14C and 14D, with the exception that the channels were wired in parallel at the channel outputs. In both the no load case (FIG. 14G) and in the resistively loaded case (FIG. 14F), the same minor variation in outputs from the different channels were observed. However, the hardwiring in parallel has created an average voltage, DC SUM, as corroborated by the mathematical average, MATH AVE, of the four traces. In the electrical loading case, 1000 ohms was applied to outputs in the individual detector/filter circuits, and 250 ohms was applied to the hardwired parallel sum. The reduction in resistance had the effect of keeping the voltage constant. The combined device achieved a four times greater current delivery capability.

Figure 14H:
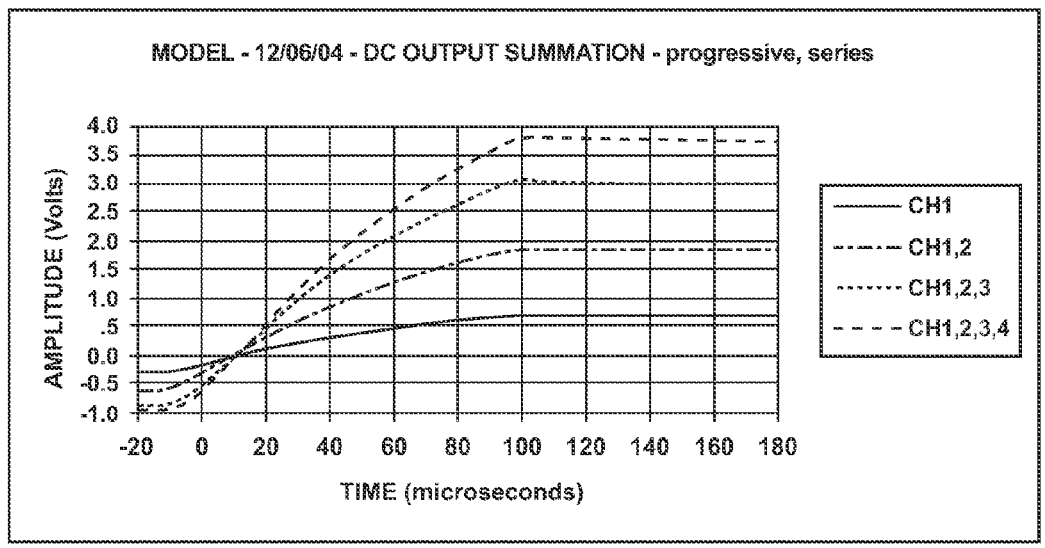
Figure 14I:
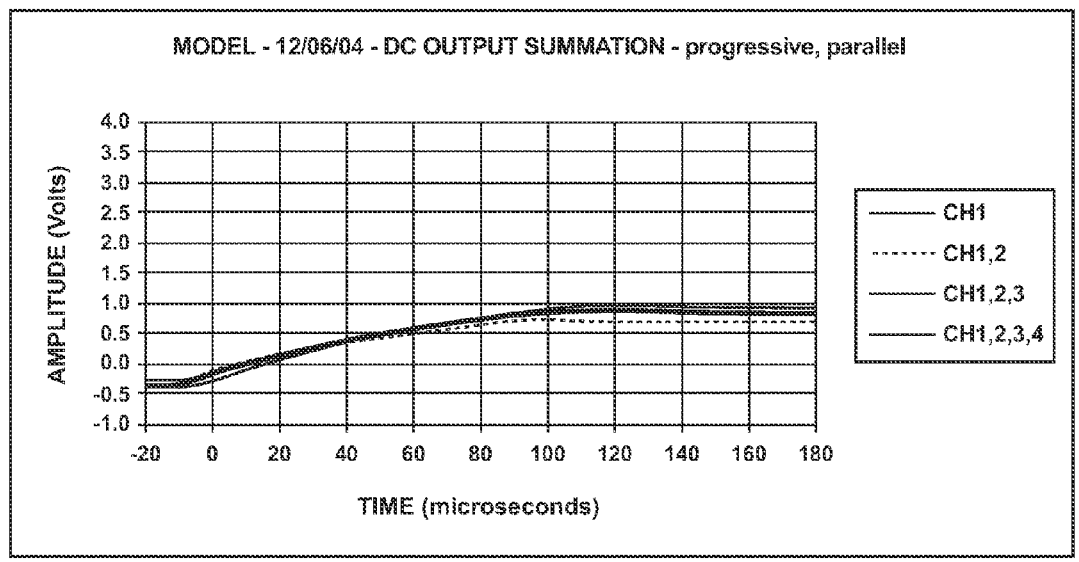

Lastly, in FIGS. 14H and 14I, the outputs of the detector/filter circuits were hardwired together, from one to four elements at a time, either in series or parallel, respectively. In FIG. 14H, adding elements simply raised the output voltage in direct relation to the number of channels. In FIG. 14I, the output voltage remained generally constant with the addition of channels, but the current delivery capability increased according to the number of channels (no current graphic shown).

It has thus been demonstrated experimentally that summation in the RF domain (transducer element output) will result in constructive and destructive interference, dependent on the phase relationship between the elements. Alternatively, by providing summation after detection and filtering, a phase independent environment is established, with only constructive interference.

The detector circuits discussed for this application might include half wave rectifiers, full wave rectifiers, voltage doublers, charge-pump devices, and the like. Filters may include series inductors, parallel capacitors, combinations of the same, and the like. Impedance matching may be accomplished through transformer devices, active or passive circuit components, or may be incorporated into the design of the detector/filter circuits. Further details on the detector/filter circuits are provided in co-pending application.

With the requirement for isotropic transducers in the receiver-stimulator, transducer size (in all lateral dimensions) should not exceed approximately 0.5 wavelengths, subject only to the amount of variation tolerated in signal strength at various elevation angles. Given a velocity of sound in normal tissue of approximately 1.5 millimeters per microseconds, at 1 MHz device sizes shall not exceed approximately 0.75 millimeters, at 0.5 MHz 1.5 millimeters, and at 250 kHz 3.0 millimeters.

Transducers in the receiver-stimulator can be positioned and located in any orientation, with respect to the axis of the transmitted acoustic beam. Transducers can be mounted in a linear manner as depicted in FIG. 13, or they can be mounted in a star pattern, a circular pattern, or a cross pattern, to recite just a few options. Further, the angular orientation of any transducer within the receiver-stimulator can be random. Anatomical conditions can be allowed to dictate the orientation of the implantable device.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An implantable receiver-stimulator device comprising:
   a transducer assembly which receives acoustic energy from an acoustic transmitter and produces electrical energy in response to the acoustic energy, wherein the electrical energy is characterized by a source impedance;
   circuitry which receives the electrical energy and produces a biologically stimulating electrical output; and
   at least two tissue contacting electrodes which receive the stimulating electrical output and deliver electrical energy to tissue, characterized by a tissue load impedance, wherein the source impedance and the tissue load impedance are matched.

2. The device of claim 1, further comprising a demodulator circuitry.

3. The device of claim 2, wherein the demodulator circuitry is configured for a 40-100% match between the source impedance and the tissue load impedance.

4. The device of claim 3, wherein the match is 100%.

5. The device of claim 2, wherein the transducer assembly comprises a plurality of individual transducer elements and wherein the demodulator circuitry further comprises a plurality of individual demodulator circuits, with the electrical energy from each transducer element fed to a demodulator circuit which produces a demodulator output, further comprising a summing circuitry which sums all of the demodulator outputs from all of the demodulator circuits to produce the biologically stimulating electrical output.

6. The device of claim 5, wherein the demodulator outputs are summed in parallel.

7. The device of claim 5, wherein the demodulator outputs are summed in series.

8. The device of claim 5, wherein the demodulator outputs are summed in a series-parallel combination.

9. The device of claim 5, wherein the transducer elements each have a size less than one-half the wavelength of an acoustic source while collectively having a size greater than one wavelength in any lateral dimension.

10. The device of claim 5, further comprising a transformer between a transducer element and a demodulator circuit configured to match the source and tissue load impedances.

11. The device of claim 5, further comprising a transformer between one or more demodulator circuits and the tissue electrodes configured to match the source and tissue load impedances.

12. The device of claim 1, wherein the transducer assembly is composed of piezoelectric transducer material with specific impedance characteristics.

13. The device of claim 12, comprising a shell having a wall surrounding an interior volume, wherein the transducer assembly and circuitry are within the interior volume and wherein at least a portion of the wall is acoustically transmissive.

14. The device of claim 13, wherein the entire shell is acoustically transmissive.

15. The device of claim 14, wherein the shell is cylindrical.

16. The device of claim 15, wherein the shell has a diameter less than 5.0 mm and a length less than 20.0 mm.

17. The device of claim 16, wherein the shell has a diameter less than 3.0 mm and a length less than 10.0 mm.

18. The device of claim 1, further comprising a transformer configured to match the source and tissue load impedances.

\* \* \* \* \*